(12) United States Patent
Tumer

(10) Patent No.: US 6,940,070 B2
(45) Date of Patent: Sep. 6, 2005

(54) IMAGING PROBE

(76) Inventor: Tumay O Tumer, 1525 Third St., Ste. C, Riverside, CA (US) 92507

( * ) Notice: Subject to any disclaimer, the term of this patent is extended or adjusted under 35 U.S.C. 154(b) by 21 days.

(21) Appl. No.: 10/279,003

(22) Filed: Oct. 24, 2002

(65) Prior Publication Data

US 2003/0081716 A1 May 1, 2003

Related U.S. Application Data

(60) Provisional application No. 60/330,597, filed on Oct. 25, 2001.

(51) Int. Cl.[7] .............................................. G01T 1/24
(52) U.S. Cl. ............................. 250/370.09; 250/370.01
(58) Field of Search ...................... 250/370.09, 370.01, 250/366, 367, 368, 369, 363.03, 363.04, 252.1, 330; 378/4, 37, 98.8

(56) References Cited

U.S. PATENT DOCUMENTS

| | | | | |
|---|---|---|---|---|
| 5,821,541 | A | * 10/1998 | Tumer | 250/370.09 |
| 6,194,715 | B1 | * 2/2001 | Lingren et al. | 250/252.1 |
| 2003/0197128 | A1 | * 10/2003 | Tumer | 250/370.09 |
| 2004/0015075 | A1 | * 1/2004 | Kimchy et al. | 600/424 |

OTHER PUBLICATIONS

Kravis, Scott D., et al., "Test Results of the Readout Electronics for Nuclear Applications (RENA) Chip Developed for Position–Sensitive Solid State Detectors," *SPIE* (Society of Photo–Optical Instrumentation Engineers), vol. 3445, Jul. 1998, pp. 374–382.

Kravis, Scott D., et. al., "A multichannel readout electronics for nuclear application RENA) chip developed for position sensitive solid state detectors," *Nuclear Instruments & Methods in Physics Research*, A 422, 1999, pp. 352–356.

Mainprize, James G., et al., "Image Quality of a Prototype Direct Conversion Detector for Digital Mammography," *Society of Photo–Optical Instrumentation Engineers*, 1999.

He, Z., et al., "3–D position sensitive CdZnTe gamma–ray spectrometers," *Nuclear Instruments & Methods in Physics Research*, A 422, 1999, pp. 173–178.

Matteson, James L., "Position–sensitive CZT detector module," *SPIE* (Society of Photo–Optical Instrumentation Engineers), vol. 3446, Jul. 1998, pp. 192–201.

(Continued)

*Primary Examiner*—Otilia Gabor
(74) *Attorney, Agent, or Firm*—Snider & Associates; Ronald R. Snider

(57) ABSTRACT

The design of a compact, handheld, solid-state and high-sensitivity imaging probe and a micro imager system is reported. These instruments can be used as a dedicated tool for detecting and locating sentinel lymph nodes and also for detecting and imaging radioactive material. The reported device will use solid state pixel detectors and custom low-noise frontend/readout integrated circuits. The detector will be designed to have excellent image quality and high spatial resolution. The imaging probes have two different embodiments, which are comprised of a pixelated detector array and a highly integrated readout system, which uses a custom multi-channel mixed signal integrated circuit. The instrument usually includes a collimator in front of the detector array so that the incident photons can be imaged. The data is transferred to an intelligent display system. A hyperspectral image can also be produced and displayed. These devices are designed to be portable for easy use.

22 Claims, 8 Drawing Sheets

OTHER PUBLICATIONS

Yasillo, Nicholas J., et al., "Design Considerations for a Single Tube Gamma Camera," *IEEE Transactions on Nuclear Science*, vol. 37, No. 2, Apr. 1990, pp. 609–615.

Bird, A.J., et al., "Images obtained with a compact gamma camera," *Nuclear Instruments & Methods in Physics Research*, A 499, 1990, pp. 480–483.

Holl, P., et al., "A Double–sided Silicon Strip Detector with Capacitive Readout and a New Method of Integrated Bias Coupling," *IEEE Transactions on Nuclear Science*, vol. 36, No. 1, Feb. 1989, pp. 251–255.

Hall, G., "Silicon Drift Chambers," *Nuclear Instruments & Methods in Physics Research*, A 273, 1988, pp. 559–564.

Aarsvold, J.N. et al., "Modular scintillation cameras: a progress report," *SPIE* (Society of Photo–Optical Instrumentation Engineers), vol. 914, Medical Imaging II, 1988, pp. 319–325.

* cited by examiner

IMAGING PROBE

CROSS REFERENCE TO PROVISIONAL PATENT APPLICATION

This application claims the benefit of the filing date of U.S. Provisional Patent Application No. 60/330,597 filed Oct. 25, 2001, the disclosure of which is incorporated herein by reference.

FIELD OF INVENTION

The focus of this work is to develop an enhanced portable imaging probe for detecting and locating sentinel lymph nodes during breast cancer surgery. It may also be used for scintimammography: diagnosis and accurate location of breast cancer tumors and their spread to surrounding tissue, especially axillary lymph nodes. It is expected to improve and expedite the sentinel node detection and locating, and enhance breast and other cancer surgery.

The instruments described can also be used for many different applications. In medical imaging, for example, they can be used for many types of x-ray and gamma ray imaging such as imaging small body organs, for molecular imaging of small animals, especially nude and scidd mice, and as an essential surgical tool. In security applications it can be used to scan people for radioactive material. In military it can be used in the field in a different portable embodiment to search and image radioactive material and/or objects that contain radioactive materials. In NDI and NDE it can be used as a portable tool to image objects for defects, cracks, etc. It may also be used to detect corrosion and cracks on aircraft and other vehicles.

BACKGROUND OF INVENTION

Single detector non-imaging probes have been in use for some time to detect and locate the sentinel lymph node(s) during breast cancer surgery. These probes have proven to be useful to the surgeon in this regard. However, they are limited in use as they do not provide an image, just a crude count rate from a 1 $cm^2$ area detector. Therefore, locating the sentinel node is not very accurate and it does not provide accurate information on the extent of the tumor. Therefore, an imaging probe with an adjustable spatial resolution by removing or exchanging the collimator will achieve significant improvement in sentinel node detecting and locating. It will also enable the imaging probe to be used for other applications such as detecting and locating primary and secondary tumors in the breast tissue and lymph nodes through scintimammography.

Recently breast imaging studies with $^{99m}Tc$ SestaMIBI and $^{201}Tl$ have demonstrated uptake by sentinel lymph nodes and malignant breast tumors but not by benign masses (except some highly cellular adenomas). Most of the results give sensitivities and specificities of about 90%, and recently equally encouraging results have been reported for $^{99m}Tc$ Methylene Diphosphonate (MDP) with a sensitivity of 92% and a specificity of 95%, even though these studies were carried out with conventional full size gamma-ray cameras which have some inherent limitations for breast imaging especially during surgery:

1. The large size of the gamma camera makes it difficult to position optimally relative to the breast.
2. Not usable during surgery due to the large size, low sensitivity and low spatial resolution.

The reported small, compact, handheld solid-state imaging probe is expected to achieve much better performance in all of these categories. It will be especially useful before, during and after surgery to locate the sentinel lymph node(s) using the drainage of the radiopharmaceutical from the tumor site to the sentinel node(s). It may also be used in the scintimammography mode to locate a lesion and its metastatic components, completely remove the cancerous tissue and verify that no cancer is left behind. Also the cancers that are not detectable by conventional mammography such as fibrocystic change and dense breasts especially in young women (≈40% between 40 and 50 year old), lack of calcifications (about 50% of all preinvasive cancers) and mammographically occult breast cancers. These, in many cases, will be identifiable by the reported system, because the method of detection relies on isotope uptake in the tumor, not on subtle differences in its radiodensity.

The instruments described here are called SenProbe (FIG. 1) and MicroImager (FIG. 7). While the SenPROBE and MicroImager systems are not directly a therapeutic tool, They have the potential to become excellent tools in monitoring the progress of surgery. Before the surgery it can be used for detecting and locating the sentinel lymph node(s), searching for malignancy in the sentinel and axillary lymph nodes, the location, size and the distribution of the tumor. During surgery the accuracy of the position and the extent of the tumor can be determined, removal of the cancerous tissue can be monitored and for the metastatic tumors the lymph nodes and the surrounding tissue can be screened, decreasing the likelihood that the physician will leave cancerous tissue behind. After the surgery the surgeon can use the SenPROBE or the MicroImager to check that the tumor is completely removed, and no residual malignant tissue remains. SenPROBE or the MicroImager may also be used in some cases before, during and/or after chemotherapy. Monitoring the tumor size will confirm that the chemotherapy treatment is effective.

SUMMARY OF INVENTION

A small, compact, portable solid state imaging probe with a built in high sensitivity tiny gamma camera as shown in FIG. 1 is discussed here as a probe to locate sentinel lymph nodes. It can also be used as a high sensitivity tool for scintimammography. The high sensitivity of the reported system is due to the very short distance to the source as the probe will be used making direct contact with the tissue, even inside a surgical cut; high Z solid state CdZnTe detector material with high quantum efficiency; and high energy resolution, about 5% to 10%, to discriminate against scattered photons and other background.

FIG. 1 is showing a drawing of the SenPROBE with one Image/Reset button and the separate LCD monitor with On/Off and Store buttons displaying two active sentinel lymph node sites. FIG. 2 is a drawing of the SenPROBE showing the internal components; honeycomb collimator (at the bottom) which is removable and interchangeable for higher sensitivity or higher spatial resolution. On top of the collimator there are the CdZnTe pixel detectors mounted on a circuit board. On the other side of the circuit board the new front-end chips will be mounted directly on the circuit board without bulky packaging to achieve the small thickness required. The data acquisition and display electronics will be housed in the color LCD monitor. The collimator is shown here as integrated into the probe. However, in practice the collimator will be easily exchanged or removed in the operating room. This will allow trade off between sensitivity and spatial resolution.

A high sensitivity SenPROBE with excellent spatial resolution is required to make this new method viable. The SenPROBE will provide the following enhancements:

1. High energy resolution, 5% to 10% at 122 keV, 3 to 5 mm thick CdZnTe pixel detectors with pixel pitch of about 2 to 3 mm with about 5×5 cm² active area will be developed.
2. Gamma rays between about 50 and 250 keV will be detected with high quantum efficiency.
3. Imaging probe size about 5×5×1 cm³ without collimator. Collimator thickness will be about 0.5 to 1 cm if needed. Most applications can be carried out at touching distance, <1 cm to the source, and will not need a collimator. Distances larger than about 1 cm will need coarse or fine collimation depending on distance.
4. An integrated circuit is developed specifically for this applications. The noise is expected to be lower and energy resolution higher. The new chip will enable compact and portable design of the imaging probe.
5. A single button will control the imaging. Each pressing will reset the image and acquire a new one. Or separate reset and image buttons can be used. Any image can be stored using the Store button on the monitor.
6. Excellent spatial resolution, about 1 mm with collimator. Without a collimator image acquisition will be fast but the image will be slightly blurred depending on the distance to the source.
7. A radio transmission system can be placed inside the SenProbe and/or the MicroImager. It can be inside the handle or attached to the instrument to relay information to the LCD monitor and eliminate connecting cable completely.
8. More then one detectors inside the instrument or two or more SenProbes and MicroImagers can be used to produce three dimensional and/or stereoscopic imaging.

The invention described comprises a medical imaging system for imaging a portion of a living organism. The living organism is treated with a radiopharmaceutical, which emits gamma ray photons. The detector contains two-dimensional array of pixels. It has an entrance aperture, which is external to the living organism and placed close or at touching distance to the portion of the living organism. The emitted gamma ray photons enter into the detector array and may scatter within the detector array.

A multi channel readout system is connected to the detector pixels. A processor is connected to the multi-channel readout system. A monitor is coupled to the processor. The monitor displays an image of the number of photons coming from the portion of the living organism imaged.

Most of the incident gamma ray photons undergo photoelectric absorption in the detector. The system includes a collimator to restrict the angle of the gamma rays incident on the detector system to determine the direction of the photons. The collimator is therefore helps to produce the image of the incident gamma rays.

The radiopharmaceuticals may contain a radio isotope(s) such as thallium-201, technetium-99m, iodine-123, iodine-131, and fluorine-18. The medical imaging system contains many pixels fabricated on the detector material. The detector (s) used can be silicon pad detectors, silicon pixel detectors, double sided silicon microstrip detectors, double sided silicon strip detectors, CdZnTe pixel detectors and CdTe pixel detectors. The detector material may be selected from Silicon, HPGe, BGO, CdWo4, CeF, NaI(Tl), CsI(Na), CsI (Tl), CdTe, CdZnTe, $HgI_2$, GaAs, and $PbI_2$.

The pixels may be fabricated on both sides of the detector. The pixels may be fabricated as ohmic and/or blocking type electrodes. The pixel pitch may vary from 0.01 to 10 mm. The medical imaging system may have several layers of detector planes.

The detector has a handle for holding the medical imaging system. The medical imaging system is also made compact and portable.

DESCRIPTION OF THE PREFERRED EMBODIMENTS

For this application, we plan to use detectors 24, 30, 82 with a thickness of 3 to 5 mm, which is well suited for photons from $^{99m}$Tc, the radionuclide most commonly used in radiopharmaceuticals. The pixel sizes will be selected from 1 to 3 mm. One side of these detectors have two-dimensional array of pixels (electrodes) normally as anodes and the other side is a single plane electrode, normally used as cathode. Another embodiment would be to make the pixels as cathodes and the backside electrode to function as anode. A bias voltage is applied between the anode and cathode where the electrons generated by an x-ray or a gamma ray are collected at the anode(s). In the main embodiment the two dimensional pixelated side faces the printed circuit board.

Figure 4:
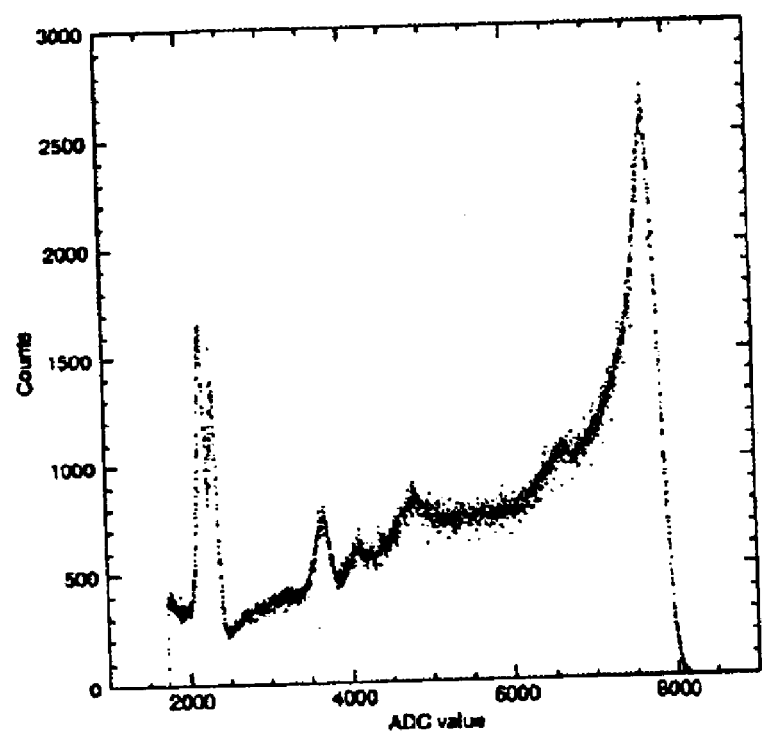
FIG. 4 is a spectrum of $^{139}$Ce measured using NOVA's CdZnTe pad detectors obtained from eV Products. The detectors are read out by the present RENA chip at or near room temperature. The shaping time is set to 1.7 μs. A Gaussian fit to the 166 keV peak ignoring the trapping tail has a width (σ) of 3.1 keV. The two partially overlapping low-energy peaks correspond to K lines (at 33.2 and 37.8 keV, respectively) of Lanthanum, the product of the Cerium decay. These lines were suppressed by shielding the source with 0.02" of copper. b) The two nuclear gamma lines at 122 and 136 keV are clearly visible A Gaussian fit to the 122 keV peak has a width of 9 keV FWHM without significant trapping tail, which is about 7% FWHM energy resolution.
Figure 5:
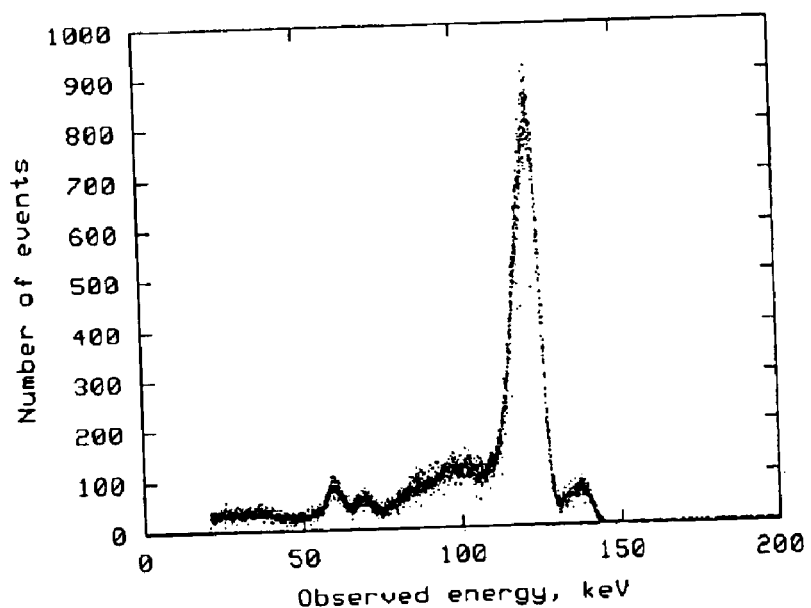
FIG. 5 is a spectrum of $^{57}$Co, measured with a new CdTe PIN detector developed by another company showing practically no charge trapping tail. Both detectors are read out by the present RENA chip at or near room temperature. The shaping time set to 1.7 μs. The two nuclear gamma lines at 122 and 136 keV are clearly visible. A Gaussian fit to the 122 keV peak has a width of 9 keV FWHM without significant trapping tail, which is about 7% FWHM energy resolution.

The energy resolution of our current CdZnTe pixel detectors (FIG. 3) 30 with 4×8 pixels and 3×3 mm$^2$ pixel pitch, read out by the RENA chip, has been measured using $^{57}$Co, $^{139}$Ce, and $^{241}$Am sources. Sample energy spectra are shown in FIG. 4 and FIG. 5.

Figure 3:
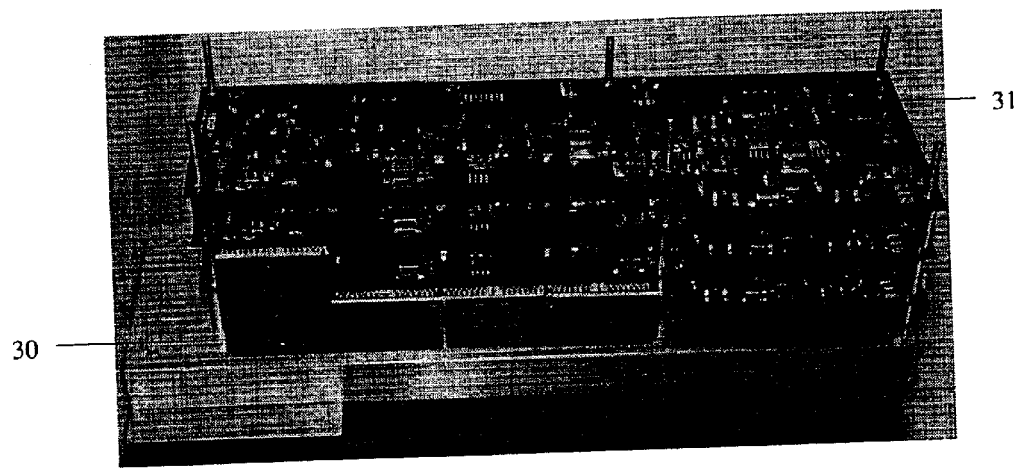
FIG. 3 is a photograph of a solid-state gamma camera. It consists of CdZnTe pixel detector units and RENA readout module boards. Each readout module board can house up to four CdZnTe detector units. In the photograph, the top module board has no detector unit, the middle one has only one detector unit, and the bottom one has four detector units.

FIG. 3 shows a photograph of a prototype solid-state gamma camera. It consists of CdZnTe pixel detector units 30 and RENA chip readout module boards 31. Each readout module board can house up to four CdZnTe detector units 30 and RENA chips. In the photograph, the top module board has no detector unit, the middle one has only one detector unit, and the bottom one has all four detector units 30.

Figure 1:
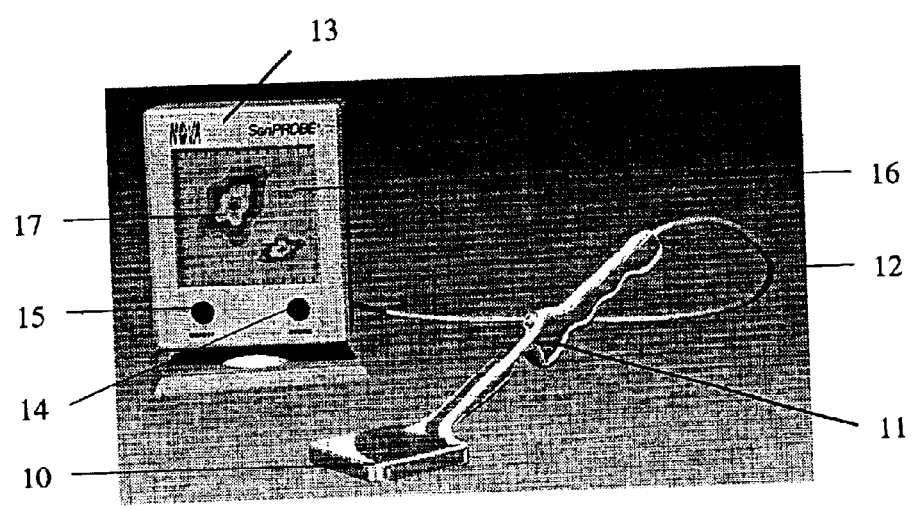
FIG. 1 is a drawing of the SenPROBE with one Image/Reset button and the separate LCD monitor with On/Off and Store buttons displaying two close active sentinel lymph node sites.
Figure 2:
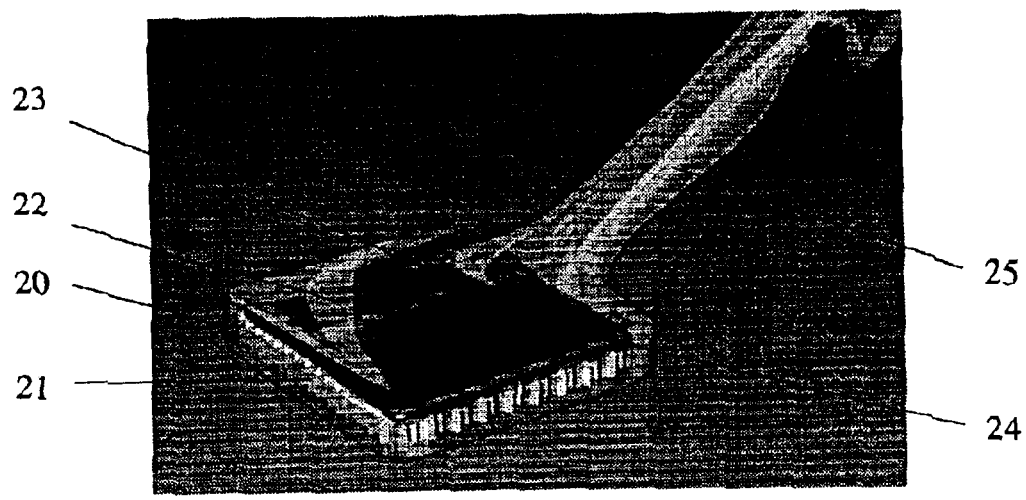
FIG. 2 is a drawing of the SenPROBE showing the internal components; honeycomb collimator (at the bottom) which is removable and interchangeable for higher sensitivity or higher spatial resolution. On top of the collimator there are the CdZnTe pixel detectors mounted on a circuit board. On the other side of the circuit board the new front-end chips will be mounted directly on the circuit board without bulky packaging to achieve the small thickness required. The data acquisition and display electronics will be housed in the color LCD monitor. The collimator is shown here as integrated into the probe. However, a removable collimator will be used, which will be easily attached or removed in the operating room. This will allow trade off between sensitivity and spatial resolution.

We plan to optimize the pixel size for the reported portable gamma camera (SenProbe). The CdZnTe pixel array 30 with 3×3 mm$^2$ pixel size shown in FIG. 3 is bulky. Therefore, new technology is used to reduce the pixel size and also miniaturize the electronics so that a compact SenProbe can be developed as shown in FIG. 1 10 and in FIG. 2 20. We plan to design the printed circuit boards to be parallel to the detector plane 22, as shown in FIG. 2, compared to the perpendicular design 31 shown in FIG. 3, to significantly reduce the SenPROBE thickness and size. Only one multi layer circuit board will be used in the probe imaging plane 22 which will house detectors on one side and the new ASICs mounted directly on the board on the other side to achieve high density and small thickness. The standard PC boards are not low noise so we will either use a ceramic carrier or a teflon board for low noise operation. The peripheral electronics, such as the ultra low noise voltage references and supplies are used in developing the instrument.

The RENA (Readout Electronics for Nuclear Application) chip 22 and 83 is used for these instruments. This chip has low noise and excellent energy resolution. Lower noise versions with more functionality and features can also be designed and used.

RENA chip 22 and 83 is a 32-channel signal processor IC for use with solid-state radiation detectors and other devices that produce a charge output. Each channel consists of an analog and a digital section; in addition, there are two isolation analog channels, one along each side of the analog channel group. RENA is self-triggered, with several different trigger modes that allow flexible operation. The flexibility is further enhanced by having eight digitally controlled shaper peaking times; this allows the chip to accommodate different charge collection times of various detectors. Up to sixteen RENA chips can be daisy-chained together with common buses for analog outputs, digital address outputs and some control signals; in this configuration the chips can be read out as a single ASIC with up to 512 channels.

FIG. 4 shows a spectrum of $^{139}$Ce measured with CdZnTe pad detectors 30 obtained from eV Products and Both detectors are read out by the RENA chip at or near room temperature. The shaping time set to 1.7 μs. A Gaussian fit to the 166 keV peak ignoring the trapping tail has a width (σ) of 3.1 keV. The two partially overlapping low-energy peaks correspond to K lines (at 33.2 and 37.8 keV, respectively) of Lanthanum, the product of the Cerium decay. These lines were suppressed by shielding the source with 0.02" of copper.

FIG. 5 shows a spectrum of $^{57}$Co using a new CdTe PIN detector developed by another company showing practically no charge trapping tail. The two nuclear gamma lines at 122 and 136 keV are clearly visible. A Gaussian fit to the 122 keV peak has a width of 9 keV FWHM without significant trapping tail, which is about 7% FWHM energy resolution.

Figure 6:
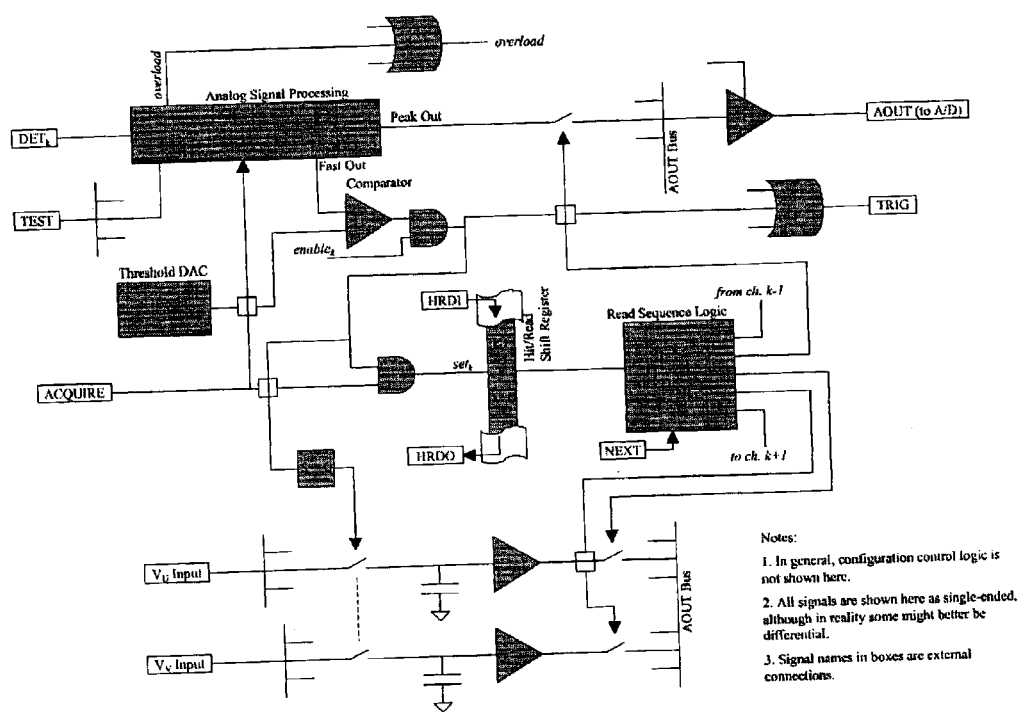
FIG. 6 is a block diagram of the new integrated circuit showing the analog circuits for one channel and some of the digital circuits.

A block diagram of a single analog channel and some digital section of an improved integrated circuit is shown in FIG. 6. The first stage of the signal path is a switched-reset integrator low noise charge sensitive amplifier. A calibration input, which is capacitatively coupled to first amplifier allows simple testing of analog channels using an external signal source. The second stage of the signal path is a polarity amplifier, which amplifies the signal from the first stage and has a control to select a positive or negative gain. The shaper, which follows the polarity amplifier, is a first order transconductance-C bandpass filter with programmable bandwidths. These bandwidths are selected through three bits in the configuration shift register. The filtered signal is peak-detected in the following stage. The peak detector is configured as such in typical operation, or as a voltage follower for diagnostic and test purposes. During readout, the peak-detected signal is isolated from the input by a switch in front of the peak detector. Two comparators sense the output level of the peak detector. The threshold comparator generates the trigger signal that is then used in the channel logic. The high-level comparator may be used, for example, to select an energy window around a nuclear line such as the 141 keV $^{99m}$Tc line. The peak-detected signals from the thirty-two channels are multiplexed onto an analog bus that is fed to an output amplifier connected to the output pad. The chip also has sparse readout capability where only the channels with valid event are read out. The new ASIC also has fast trigger output for timing applications and a hit/read shift register to provide the number and address of the channels with valid event.

The SenPROBE (FIG. 1 10 and FIG. 2 20) will be developed to have an active area of about 5×5 cm$^2$. The most likely area will be about 4"×4". The total thickness of the SenPROBE will depend on the collimator 21 thickness and the number of circuit boards 22. The collimator 21 is expected to be about 5 to 10 mm thick depending on spatial resolution required. The hole diameter will be selectable from about 1 mm to 3 mm to allow for fast or fine resolution imaging as required. The collimator 21 will be designed to be interchangeable so that the operator or the surgeon can change it as required. The CdZnTe detector 24 thickness will be about 3 to 5 mm. The probe will have a handle 11 connected to the display or monitor via a cable 13. The cable 13 can be eliminated if a radio or microwave connection between the probe and the monitor is established. The monitor 13 has a display screen 16 and it can use a microprocessor or computer to process data obtained from the probe and display the image 17 on the display screen 16. The display or monitor 13 has buttons to control the instrument such as the ON/OFF button 15 and STORE button 14. Other buttons such as RESET and IMAGE (not shown) may also be used.

Up to four circuit boards can be deployed. The first one will house the detectors 24 on the bottom side and the RENA chips 22 on the top side so that the pixels can be connected through short, low capacitance leads to achieve high energy resolution. The second circuit board will house the data interface to the data acquisition board and will be housed in the handle 25 of the probe. The third board will contain the power supplies, the data acquisition, and display interface circuits and it will be housed inside the color LCD display monitor 13. The fourth circuit board will have the onboard microprocessor and the display driver. The entire electronics will be run by high-power rechargeable Ni-MH or Li ion or similar batteries.

The display 16 will be made from a large size color LCD. The display will show a contour plot of the received image 17 (counts per pixel) from the detector in real time. The operator will decide how long to acquire the image. The display will also have a ruler on all sides 16 corresponding to the active dimensions of the detector. On the sides of the SenProbe 10 and 20 there will be a corresponding ruler. This will allow the surgeon to make marks on the tissue corresponding to the center and size of the tumor.

Figure 7:
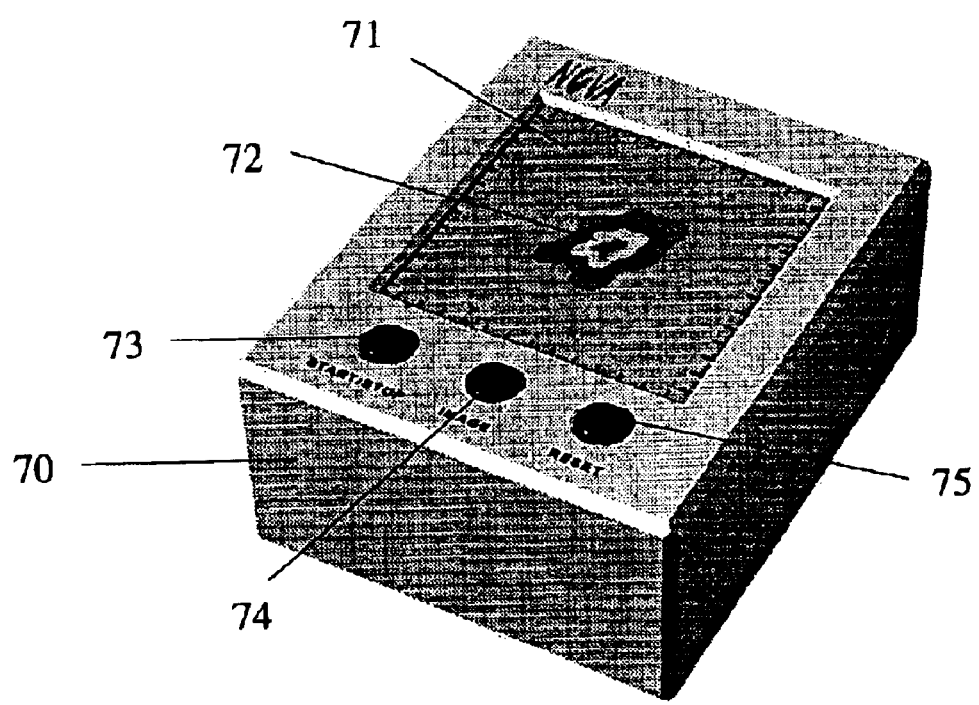
FIG. 7 is a drawing of the MicroImager showing the control buttons, the display of an imaged tumor, and the ruler showing the location of the tumor.
Figure 8:
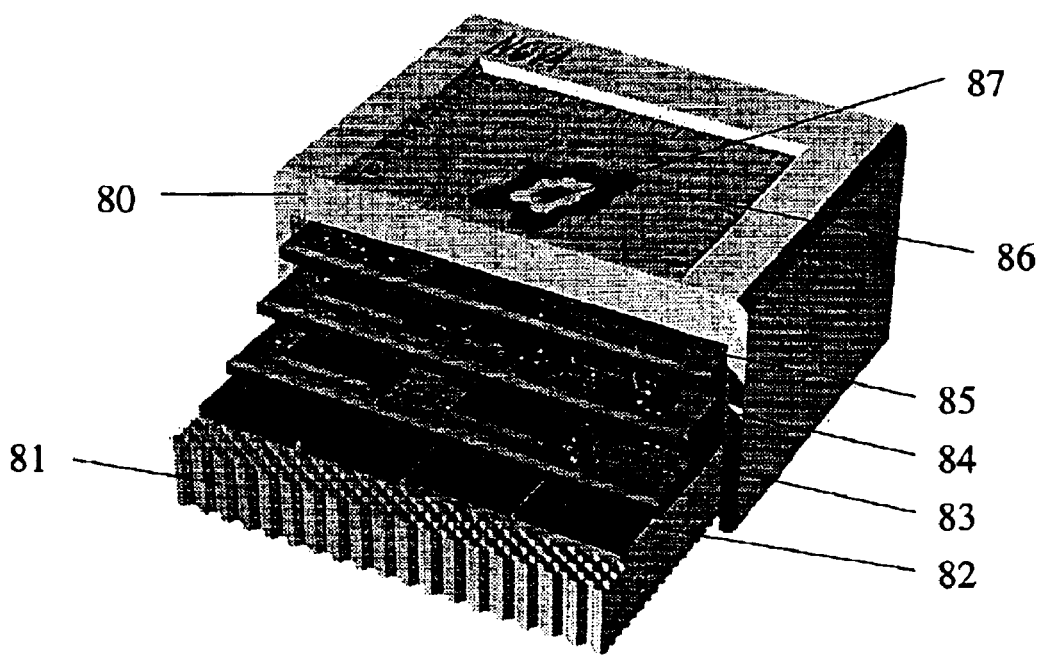
FIG. 8 is a drawing of the MicroImager showing the internal components; honeycomb collimator (at the bottom), the CdZnTe pixel detectors on top of the collimator and the circuit boards for the front-end, data acquisition and display electronics, respectively.

In another embodiment called MicroImager 70 and 80 in FIG. 7 and FIG. 8 a small, compact, portable solid state gamma camera is shown which is a different embodiment to SenProbe shown in FIG. 1 10. This embodiment may be used as a complementing modality to mammography to solve the problems stated above.

MicroImager 70 contains a display 71 an several buttons to control the instrument. These buttons can be START/STOP button 73, IMAGE button 74 and a RESET button 75. A drawing of the MicroImager showing a display of a tumor 72 is shown in FIG. 7. The display 71 has ruler markings allowing easy determination of the location of the tumor 72. FIG. 8 displays a drawing of the MicroImager 80 showing the internal components; honeycomb collimator 81 at the bottom, the CdZnTe pixel detectors 82 on top of the collimator and the circuit boards 83, 84 and 85 for the front-end, data acquisition and display electronics, respectively.

The MicroImager (FIG. 8) 80 will be developed to have an active area of about 3"×3" to about 5"×5". The most likely area will be about 4"×4". The total thickness of the MicroImager will depend on the collimator thickness and the number of circuit boards. The collimator 81 is expected to be about 1 to 10 mm thick. The hole diameter will be selectable from about 2 mm to 5 mm to allow for fast or fine resolution imaging as required. The collimator 81 will be designed to be interchangeable so that the operator or the surgeon can change it as required. The CdZnTe detector thickness will be about 2 to 5 mm.

We plan to build three circuit boards (FIG. 8). The first one will house the detectors 82 on the bottom side and the RENA ASICs 83 on the top side so that the pixels can be connected through short, low capacitance leads to achieve high energy resolution. The middle circuit board 84 will house the power supplies, the data acquisition, and interface circuits. The top circuit board 85 will have the onboard microprocessor and the display driver. The entire electronics will be run by high-power rechargeable Ni-MH batteries.

The display 86 will be made from a large size LCD with dimensions as close to the active area as allowed by the real estate available on the top surface of the MicroImager. The display will show a contour plot 87 of the received signal (counts per pixel) from the detector in real time. The operator then can decide how long to acquire the image. The display will also have a ruler on all sides corresponding to the active dimensions of the detector. On the sides of the MicroImager 80 there will be a corresponding ruler. This will allow the surgeon to make marks on the tissue corresponding to the center and size of the tumor. After the MicroImager is removed the lines can be joined to mark the location of the lesion so that it can be easily located and removed.

The position resolution will depend on the collimator 81 used. The best position resolution achievable is expected to be about 1 mm.

There are three function buttons, START/STOP 73, IMAGE 74, and RESET 75. START/STOP will turn the detector on and off, IMAGE button will initiate the image acqusition and the RESET button will clear the image. The can be other buttons if needed. An image memory will store about 32 or more images, which can be downloaded later to a computer if needed.

What is claimed:

1. A method of imaging a portion of a human body, the method comprising the steps of:

providing a radiopharmaceutical to said portion of said human body, said radiopharmaceutical producing radiation;

positioning a detection system proximate to said portion of said human body, wherein said detection system is comprised of a compact and portable detector, wherein said detector comprised of two dimensional plurality of pixels;

determining a direction and an energy for a portion of said radiation entering said detection system from a plurality of pixels;

processing said direction and energy data for said portion of radiation; and displaying an image in real time of said portion of said human body, wherein said image is based on said processed direction and energy data.

2. The method of claim 1, wherein said portion of said human body is an organ.

3. The method of claim 1, wherein said portion of said human body is a breast.

4. The method of claim 1, further comprising using the image to determine the position of at least one section of said portion of the said living organism which emits gamma rays at a higher rate than the background and locating said section using rulings on a display.

5. The method of claim 1, wherein said imaging method produces a hyperspectral image.

6. The method of claim 1, further comprising a step of detecting at least one section of said portion of the said living organism which has higher uptake of the said radiopharmaceutical over the rest of the said portion.

7. The method of claim 1, wherein said imaging method uses a collimator to restrict the angle of the radiation for controlling the direction of the radiation that enters its aperture.

8. The medical imaging system of claim 1, wherein said radiation emitted from a radiopharmaceutical is selected from the group of particles consisting of photon, electron, positron, proton and alpha particle.

9. A medical imaging system for imaging a portion of a living organism, said portion treated with a radiopharmaceutical said radiopharmaceutical emitting radiation, comprising:

a detector comprised of a plurality of two-dimensional pixels, wherein an entrance aperture of said detector is external to said living organism and proximate to said portion of said living organism, wherein said emitted radiation enter into said detector and are absorbed within said detector;

a multi channel readout system coupled to at least one said pixel of said detector;

a processor coupled to said multi-channel readout system; and a monitor coupled to said processor, said monitor displaying an image of radiation coming from the said portion of said living organism in real time.

10. The medical imaging system of claim 9; wherein a portion of said emitted radiation enters the said detector, makes a photoelectric interaction wherein a position of interaction is determined from energy deposited inside at least one of the said pixels of the said detector and wherein the position of interaction is used to determine direction of the incident radiation.

11. The medical imaging system of claim 9, further comprising a collimator to restrict an angle of radiation incident on the said detector to determine the direction of the incident radiation.

12. The medical imaging system of claim 9, wherein said radiopharmaceutical is tagged with a radioactive material which is selected from the group consisting of thallium-201, technetium-99m, iodine-123, iodine-131, and fluorine-18.

13. The medical imaging system of claim 9, further comprising a handle for holding the said medical imaging system.

14. The medical imaging system of claim 9, wherein said detector is selected from at least one of the detector types including pad detectors, pixel detectors, double sided microstrip detectors, double sided strip detectors, and double sided pixel detectors.

15. The medical imaging system of claim 9, wherein both sides of the said detector contain said plurality of pixels.

16. The medical imaging system of claim 9, wherein said pixels are made from ohmic type electrodes.

17. The medical imaging system of claim 9, wherein said pixels are made from blocking type electrodes.

18. The medical imaging system of claim 9, wherein said plurality of pixels have a pitch varying from 0.01 to 10 mm.

19. The medical imaging system of claim 9, wherein there is at least one detector plane.

20. The medical imaging system of claim 9, wherein said detector material is selected from the group of detector materials consisting of Silicon, HPGe, BGO, CdWo4, CsF, NaI(Tl), CsI(Na), CsI(Tl), CdTe, CdZnTe, $HgI_2$, GaAs, and $PbI_2$.

21. The medical imaging system of claim 9, wherein said imaging system is made compact and portable.

22. The medical imaging system of claim 9, wherein said radiation emitted from a radiopharmaceutical is selected from the group of particles consisting of photon, electron, positron, proton and alpha particle.

* * * * *